US007943644B2

(12) United States Patent
Uhr et al.

(10) Patent No.: US 7,943,644 B2
(45) Date of Patent: May 17, 2011

(54) STABILIZATION OF IODINE-CONTAINING BIOCIDES BY MEANS OF SPECIAL AZOLE COMPOUNDS

(75) Inventors: Hermann Uhr, Leverkusen (DE); Johannes Kaulen, Odenthal (DE); Thomas Jaetsch, Köln (DE); Peter Spetmann, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 18 days.

(21) Appl. No.: 12/281,163

(22) PCT Filed: Feb. 21, 2007

(86) PCT No.: PCT/EP2007/001480
§ 371 (c)(1),
(2), (4) Date: Nov. 10, 2008

(87) PCT Pub. No.: WO2007/101549
PCT Pub. Date: Sep. 13, 2007

(65) Prior Publication Data
US 2009/0192219 A1    Jul. 30, 2009

(30) Foreign Application Priority Data

Mar. 6, 2006    (DE) .................. 10 2006 010 199

(51) Int. Cl.
*A61K 31/41*    (2006.01)
*A61K 47/00*    (2006.01)
(52) U.S. Cl. ......... 514/359; 514/361; 514/381; 514/769
(58) Field of Classification Search .................. 514/359, 514/361, 381, 769
See application file for complete search history.

(56) References Cited

U.S. PATENT DOCUMENTS

| | | | | |
|---|---|---|---|---|
| 2,739,922 | A | * | 3/1956 | Shelanski ...................... 524/548 |
| 4,276,211 | A | | 6/1981 | Singer et al. ......... 260/29.6 MN |
| 4,297,258 | A | | 10/1981 | Long, Jr. .............. 260/29.6 MN |
| 4,552,885 | A | | 11/1985 | Gabriele et al. ............... 514/316 |
| 5,051,256 | A | * | 9/1991 | Barnes .......................... 424/402 |
| 6,143,204 | A | | 11/2000 | Lutz et al. ...................... 252/384 |
| 6,353,021 | B1 | | 3/2002 | Gaglani et al. ................ 514/478 |
| 6,472,424 | B1 | | 10/2002 | Gaglani et al. ................ 514/478 |
| 6,946,427 | B2 | * | 9/2005 | Lutz et al. ..................... 504/140 |
| 2006/0013833 | A1 | | 1/2006 | Bartko .......................... 424/400 |
| 2007/0128246 | A1 | * | 6/2007 | Hossainy et al. ............. 424/423 |

FOREIGN PATENT DOCUMENTS

| WO | 98/22543 | 5/1998 |
|---|---|---|
| WO | 99/29176 | 6/1999 |
| WO | 00/16628 | 3/2000 |
| WO | 2007/028527 | 3/2007 |

OTHER PUBLICATIONS

Nomiya, Kenji, et al, "Synthesis and Crystal Structure of Coinage Metal (I) Complexes with Tetrazole (Htetz) and Triphenylphospine Ligands, and Their Antimicrobial Activities. A Helical Polymer of Silver (I) Complex [Ag(tetz)(PPh3)2]n and Monomeric Gold (I) Complex [Au(tetz)(PPh3)]," Inorganica Chimica Acta, vol. 298, pp. 24-32 (2000).*

Abstract of CS Patent No. 276253 B6 (Apr. 11, 1991) STN Search Notes at L3, Answer 15.*

* cited by examiner

*Primary Examiner* — Raymond J Henley, III
(74) *Attorney, Agent, or Firm* — Nicanor A. Kohncke

(57) ABSTRACT

Specific azole compounds are outstandingly suitable for stabilizing iodine-containing biocides in industrial materials, more particularly in paints based on alkyd resin.

14 Claims, No Drawings

STABILIZATION OF IODINE-CONTAINING BIOCIDES BY MEANS OF SPECIAL AZOLE COMPOUNDS

CROSS REFERENCE TO RELATED PATENT APPLICATIONS

The present patent application claims the right of priority under 35 U.S.C. §119 (a)-(d) and 35 U.S.C. §365 of International Application No. PCT/EP2007/001480, filed 21 Feb. 2007, which was published in German as International Patent Publication No. WO 2007/101549 A1 on 13 Sep. 2007, which is entitled to the right of priority of German Patent Application DE 10 2006 010 199.5 filed on 6 Mar. 2006.

The invention relates to the use of specific known azole compounds as stabilizers of iodine-containing biocides, and also to active compound formulations, concentrates and industrial products comprising iodine-containing biocide and specific azole compounds.

Iodine-containing biocides are generally employed in order to protect industrial materials from decomposition/destruction and visual alteration by fungi, bacteria and algae, preferably by fungi. Also used here besides iodoalkynyl compounds are active compounds in which one or more iodine atoms are attached at double bond systems, but also to singly bonded carbon atoms.

Features common to all iodine-containing biocides are firstly that on exposure to light they lead to a yellowing accompanied by loss of active compound and activity and secondly that in many application forms, but especially in solvent-based formulations, paints, stains or varnishes, even without exposure to light, they are chemically unstable, which is manifested in a degradation of the active compound, with the result of reduced biological activity.

The chemical degradation is particularly severe in the presence of transition metal compounds, which are used preferentially as dryers (siccatives) in paints containing alkyd resin. Particularly noteworthy here are cobalt-containing dryers, although the alternatively and in some cases additionally used lead, manganese and vanadium dryers also lead to severe active compound degradation.

As well as the dryers, there are a series of further constituents leading, in varying intensities, to degradation of iodine-containing biocides in paints, varnishes, primers, impregnating systems, stains and active compound formulations. While the destabilizing effect is still relatively weak in the case of the solvents typically used, the other typical components of a paint formulation, such as in-process additives, plasticizers, colour pigments, anti-settling agents, thixotropic agents, corrosion inhibitors, anti-skinning agents and binders, for example, show more or less strongly pronounced destabilizing effects.

Surprisingly it has now been found that through the use of particular azole compounds, in particular from the group of imidazoles, triazoles and tetrazoles, it is possible to stabilize iodine-containing biocides both from chemical and light-induced degradation, thereby making it possible to prevent the above-described drawbacks such as colour changes and chemical degradation.

The azoles for use in accordance with the invention, in particular from the group of imidazoles, triazoles and tetrazoles, are known; however, their use for stabilizing iodine-containing biocides has not previously been described.

There are already known methods of preventing the degradation of halopropargyl compounds in transition metal-containing alkyd resin paints. WO 98/22543, for example, describes the use of chelating reagents.

Also known are transition metal-containing alkyd resin paints in which halopropargyl compounds are stabilized by means of organic epoxides (cf. WO 00/16628).

There have also already been descriptions of processes for suppressing the light-induced degradation of active antifungal compounds, such as iodopropargyl butylcarbamate among others, by addition of tetraalkylpiperidine compounds and/or UV absorbers (cf. EP-A 0 083 308).

The addition of epoxy compounds is intended to reduce the discoloration of iodoalkyne compounds, such as IPBC (cf. U.S. Pat. No. 4,276,211 and U.S. Pat. No. 4,297,258).

Also described, furthermore, have been synergistic mixtures of epoxides with UV absorbers (cf. WO 99/29176) and with benzylidenecamphor derivatives (cf. U.S. Pat. No. 6,472,424) which likewise exhibit reduced yellowing.

The stabilizing activity of the aforementioned stabilizers, however, is not always sufficient, and is hampered by performance drawbacks. Thus it is observed in particular that the drying times of the paints are significantly prolonged, which in many cases is unacceptable to the user. Moreover, the inhibition of the coloration is not always satisfactory.

The present invention accordingly provides active compound mixtures comprising at least one iodine-containing biocide and at least one azole compound of the general formula (I) or tautomer thereof,

in which
$R^1$ is hydrogen, hydroxyl, mercapto or optionally substituted amino
and
X, Y and Z independently of one another are N or C—$R^2$,
in which
$R^2$ is hydrogen, hydroxyl, mercapto or optionally substituted amino.

Preference is given to mixtures comprising at least one iodine-containing biocide and at least one azole compound of the formula (I) or tautomer thereof
in which
$R^1$ is hydrogen, hydroxyl, mercapto, amino, $C_1$-$C_3$-alkylamino or di-$C_1$-$C_3$-alkylamino
and
X, Y and Z independently of one another are N or C—$R^2$
and
$R^2$ is hydrogen, hydroxyl, mercapto, amino, $C_1$-$C_3$-alkylamino or di-$C_1$-$C_3$-alkylamino.

The radicals indicated in the respective definitions and preferred and particularly preferred definitions may, independently of the particular combination indicated, be replaced in any desired way, including replacement by radical definitions of other combinations. Moreover, radical definitions from each preference range may also be omitted.

Particular preference is given to mixtures of the invention which comprise at least one of the following imidazoles, triazoles or tetrazoles:
2-aminoimidazole,
4-aminoimidazole,
2-hydroxyimidazole,
4-hydroxyimidazole,
2-mercaptoimidazole,
4-mercaptoimidazole, 2-imidazolin-4-one,
4-amino-2-hydroxyimidazole,
4-amino-2-mercaptoimidazole,
3-amino-1,2,4-triazole,
3-hydroxy-1,2,4-triazole,
3-mercapto-1,2,4-triazole,
3-amino-5-hydroxy-1,2,4-triazole,
3-amino-5-mercapto-1,2,4-triazole,
3,5-diamino-1,2,4-triazole,
3-hydroxy-5-mercapto-1,2,4-triazole,
3,5-dihydroxy-1,2,4-triazole,
3,5-dimercapto-1,2,4-triazole,
5-amino-1,2,3,4-tetrazole,
5-hydroxy-1,2,3,4-tetrazole,
5-mercapto-1,2,3,4-tetrazole.

The iodine-containing biocides present in the mixtures of the invention are preferably iodoalkynyl compounds or compounds in which one or more iodine atoms are attached to double bond systems, or compounds in which one or more iodine atoms are attached to singly bonded carbon atoms.

With particular preference the iodine-containing active compounds are the following compounds: 3-iodo-2-propynylpropyl carbamate, 3-iodo-2-propynylbutyl carbamate (IPBC), 3-iodo-2-propynyl-m-chlorophenyl carbamate, 3-iodo-2-propynylphenyl carbamate, 3-iodo-2-propynyl 2,4,5-trichloro-phenyl ether, 3-iodo-2-propynyl 4-chlorophenyl formal (IPCF), di(3-iodo-2-propynyl)hexyl dicarbamate, 3-iodo-2-propynyloxyethanol ethylcarbamate, 3-iodo-2-propynyloxyethanol phenyl carbamate, 3-iodo-2-propynylthioxothioethyl carbamate, 3-iodo-2-propynylcarbamic ester (IPC), N-iodpropargyloxycarbonylalanine, N-iodopropargyloxycarbonylalanine ethyl ester, 3-(3-iodo-propargyl)benzoxazol-2-one, 3-(3-iodopropargyl)-6-chlorobenzoxazol-2-one, diiodomethyl p-tolyl sulphone, diiodomethyl p-chlorophenyl sulphone, 3-iodo-2-propynyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-hexylcarbamate, 3-iodo-2-propynyl cyclohexylcarbamate.

The mixtures of the invention in general contain 0.01%-70% by weight of at least one iodine-containing biocide and 0.001%-50% by weight of at least one azole compound of the formula (I), preferably 0.05%-60% by weight of at least one iodine-containing biocide and 0.005%-40% by weight of at least one azole compound of the formula (I), and with particular preference 0.1%-50% by weight of at least one iodine-containing biocide and 0.01%-30% by weight of at least one azole compound of the formula (I).

The mixtures of the invention can be prepared by mixing together the individual components as a function of their respective physical and/or chemical properties, without additives, or converting them into the typical formulations, such as solutions, emulsions, suspensions, powders, foams, pastes, granules, aerosols and ultra-fine encapsulations in polymeric substances.

The mixtures of the invention are suitable for protecting industrial materials. Industrial materials in the present context are non-living materials which have been prepared for use in industry. The industrial materials are, for example, adhesives, sizes, paper and cardboard, textiles, leather, wood, wood-based materials, coating materials and plastics articles, cooling lubricants and other materials which may be infested or decomposed by microorganisms.

Additionally provided is the use of the mixtures of the invention for protecting industrial materials against infestation and/or destruction by microorganisms.

Examples of microorganisms which may bring about degradation or alteration of the industrial materials include bacteria, fungi, yeasts, algae and slime organisms. The active compounds of the invention act preferably against fungi, more particularly moulds, wood-discolouring and wood-destroying fungi (Basidiomycetes) and also against slime organisms and bacteria.

Microorganisms of the following genera may be mentioned by way of example:
*Alternaria*, such as *Alternaria tenuis*,
*Aspergillus*, such as *Aspergillus niger*,
*Chaetomium* such as *Chaetomiurn globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.

Depending on their respective physical and/or chemical properties, the mixtures of the invention can furthermore be converted into the typical formulations, such as solutions, emulsions, suspensions, powders, foams, pastes, granules, aerosols and ultrafine encapsulations in polymeric substances.

These formulations can be prepared in a known manner, for example by mixing the active compounds with extenders, that is, liquid solvents, liquefied gases under pressure, and/or solid carriers, if appropriate with the use of surfactants, that is emulsifiers and/or dispersants and/or foam-formers. If the extender used is water, it is also possible to use for example organic solvents as auxiliary solvents. Essentially, suitable liquid solvents are: aromatics, such as xylene, toluene or alkylnaphthalenes, chlorinated aromatics or chlorinated aliphatic hydrocarbons, such as chlorobenzenes, chloroethylene or methylene chloride, aliphatic hydrocarbons, such as cyclohexane or paraffins, for example mineral oil fractions, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water. By liquefied gaseous extenders or carriers are meant liquids which are gaseous at ambient temperature and under atmospheric pressure, for example aerosol propellants, such as halogenated hydrocarbons and butane, propane, nitrogen and carbon dioxide. Suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates. Suitable solid carriers for granules are: for example crushed and fractionated natural rocks such as calcite, marble, pumice, sepiolite and dolomite, and synthetic granules of organic and inorganic meals, and granules of organic material such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other possible additives are mineral and vegetable oils.

It is possible to use colourants such as inorganic pigments, for example iron oxide, titanium oxide and Prussian blue, and organic dyes, such as alizarin dyes, azo dyes and metal phthalocyanine dyes, and trace nutrients such as salts of iron, manganese, boron, copper, cobalt, molybdenum and zinc.

The formulations generally comprise between 0.1 and 95 percent by weight of active compound, preferably between 2 and 75 percent by weight.

The present invention further provides microbicidal compositions based on the mixtures of the invention and comprising at least one solvent or diluent and also, if appropriate, processing auxiliaries and, if appropriate, further antimicrobially active compounds. In this case, the active compounds may be present herein either in dissolved form or as suspensions or emulsions. The solvents or diluents are either water or all customary organic solvents.

The efficacy and the activity spectrum of the mixtures of the invention and of the compositions preparable therefrom can be increased by adding, if appropriate, further antimicrobial compounds, fungicides, bactericides, herbicides, insecticides or other active compounds, so as to widen the spectrum of activity or to obtain particular effects. These mixtures may have an even wider activity spectrum.

In many cases, synergistic effects are obtained, i.e. the activity of the mixture is greater than the activity of the individual components. The following compounds, for example, are found to be particularly favorable co-components:

triazoles such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeconazole, (±)-cis-1-(4-chlorophenyl)-2-(1H-1,2,4-triazol-1-yl)cycloheptanol, 2-(1-tert-butyl)-1-(2-chlorophenyl)-3-(1,2,4-triazol-1-yl) propan-2-ol, tebuconazole, tetraconazole, triadimefon, triadimenol, triapenthenol, triflumizole, triticonazole, uniconazole and their metal salts and acid adducts;

imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chloro-phenoxy)-3,3-dimethylbutan-2-one, and their metal salts and acid adducts;

pyridines and pyrimidines such as:
ancymidol, buthiobate, fenarimol, mepanipyrin, nuarimol, pyvoxyfur, triamirol;

succinate dehydrogenase inhibitors such as:
benodanil, carboxim, carboxim sulphoxide, cyclafluramid, fenfuram, flutanil, furcarbanil, furmecyclox, mebenil, mepronil, methfuroxam, metsulfovax, nicobifen, pyracarbolid, oxycarboxin, Shirlan, Seedvax;

naphthalene derivatives such as:
terbinafine, naftifine, butenafine, 3-chloro-7-(2-aza-2,7,7-trimethyloct-3-en-5-yne);

sulphenamides such as:
dichlofluanid, tolylfluanid, folpet, fluorofolpet, captan, captofol;

benzimidazoles such as:
carbendazim, benomyl, fuberidazole, thiabendazole or their salts;

morpholine derivatives such as:
aldimorph, dimethomorph, dodemorph, falimorph, fenpropidin, fenpropimorph, tridemorph, trimorphamid and their arylsulphonate salts such as, for example, p-toluenesulphonic acid and p-dodecylphenylsulphonic acid;

benzothiazoles such as:
2-mercaptobenzothiazole;

benzothiophene dioxides such as:
N-cyclohexyl-benzo[b]thiophenecarboxamide S,S-dioxide;

benzamides such as:
2,6-dichloro-N-(4-trifluoromethylbenzyl)benzamide, tecloftalam;

boron compounds such as:
boric acid, boric esters, borax;

formaldehyde and formaldehyde-releasing compounds such as:
benzyl alcohol mono(poly)hemiformal, 1,3-bis(hydroxymethyl)-5,5-dimethylimidazolidine-2,4-dione (DMDMH), bisoxazolidine, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis-(hydroxymethyl)urea, dazomet, dimethylolurea, 4,4-dimethyloxazolidine, ethylene glycol hemiformal, 7-ethylbicyclooxazolidine, hexahydro-S-triazine, hexamethylenetetramine, N-hydroxymethyl-N'-methylthiourea, methylenebismorpholine, sodium N-(hydroxymethyl)glycinate, N-methylolchloroacetamide, oxazolidine, paraformaldehyde, taurolin, tetrahydro-1,3-oxazine, N-(2-hydroxypropyl) aminemethanol, tetramethylolacetylenediurea (TMAD);

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethyleneisothiazolinone, 4,5-benzoisothiazolinone;

aldehydes such as:
cinnamaldehyde, formaldehyde, glutardialdehyde, β-bromocinnamaldehyde, o-phthaldialdehyde;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzyldimethyl-dodecylammonium chloride, dichlorobenzyldimethylalkylammonium chloride, didecyldimethyl-ammonium chloride, dioctyldimethylammonium chloride, N-hexadecyltrimethylammonium chloride, 1-hexadecylpyridinium chloride, iminoctadine tris(albesilate);

iodine derivatives such as:
diiodomethyl p-tolyl sulphone, 3-iodo-2-propynyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;

phenols such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxy-benzoate, ethyl p-hydroxybenzoate, propyl p-hydroxybenzoate, butyl p-hydroxybenzoate, octyl p-hydroxybenzoate, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)-phenol and their alkali metal salts and alkaline earth metal salts;

microbicides with an activated halogen group such as:
bronopol, bronidox, 2-bromo-2-nitro-1,3-propanediol, 2-bromo-4'-hydroxyacetophenone, 1-bromo-3-chloro-4,4,5,5-tetramethyl-2-imidazolidinone, β-bromo-β-nitrostyrene, chloracetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl (2-chlorocyanovinyl) sulphone, phenyl (1,2-dichloro-2-cyanovinyl) sulphone, trichloroisocyanuric acid;

pyridines such as:
1-hydroxy-2-pyridinethione (and their Cu, Na, Fe, Mn, Zn salts), tetrachloro-4-methyl-sulphonylpyridine, pyrimethanol, mepanipyrim, dipyrithion, 1-hydroxy-4-methyl-6-(2,4,4-trimethylpentyl)-2(1H)-pyridine;

methoxyacrylates or similar such as:
azoxystrobin, dimoxystrobin, fluoxastrobin, kresoxim-methyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]amino]oxy]methyl]phenyl]-3H-1,2,4-triazol-3-one (CAS No. 185336-79-2);

metal soaps such as:
salts of the metals tin, copper and zinc with higher fatty acids, resin acids, naphthenoic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:
salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate;

oxides such as:
oxides of the metals tin, copper and zinc, such as, for example, tributyltin oxide, $Cu_2O$, CuO, ZnO;

oxidizing agents such as:
hydrogen peroxide, peracetic acid, potassium persulphate;

dithiocarbamates such as:
cufraneb, ferban, potassium N-hydroxymethyl-N'-methyldithiocarbamate, sodium dimethyl-dithiocarbamate, potassium dimethyldithiocarbamate, mancozeb, maneb, metam, metiram, thiram, zineb, ziram;

nitriles such as:
2,4,5,6-tetrachloroisophthalonitrile, disodium cyanodithioimidocarbamate;

quinolines such as:
8-hydroxyquinoline and their copper salts;

other fungicides and bactericides such as:
bethoxazin, 5-hydroxy-2(5H)-furanone, 4,5-benzodithiazolinone, 4,5-trimethylenedithiazolinone, N-(2-p-chlorobenzoylethyl)hexaminium chloride, 2-oxo-2-(4-hydroxyphenyl) acetohydroxy-cinnamoyl chloride, tris-N-(cyclohexyldiazeniumdioxy)-aluminium, N-(cyclohexyldiazenium-dioxy)-tributyltin or its potassium salts, bis-N-(cyclohexyldiazeniumdioxy)-copper; iprovalicarb, fenhexamide, spiroxamine, carpropamid, diflumetorin, quinoxyfen, famoxadone, polyoxorim, acibenzolar S-methyl, furametpyr, thifluzamide, methalaxy-M, benthiavalicarb, metrafenon, cyflufenamid, tiadinil, tea tree oil, phenoxyethanol, Ag, Zn or Cu-containing zeolites alone or incorporated into polymeric materials.

Very especially preferred are mixtures with azaconazole, bromuconazole, cyproconazole, dichlobutrazol, diniconazole, diuron, hexaconazole, metaconazole, penconazole, propiconazole, tebuconazole, dichlofluanid, tolylfluanid, fluorfolpet, methfuroxam, carboxin, N-cyclohexyl-benzo[b]thiophenecarboxamide S,S-dioxide, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, dichloro-N-octylisothiazolinone, mercaptobenzothiazole, thiocyanatomethylthiobenzothiazole, thiabendazole, benzoisothiazolinone, N-(2-hydroxypropyl)aminoethanol, benzyl alcohol (hemi)formal, N-methylolchloroacetamide, N-(2-hydroxypropyl) aminemethanol, glutaraldehyde, omadine, Zn-omadine, dimethyl dicarbonate, 2-bromo-2-nitro-1,3-propanediol, 3-iodo-2-propynyl n-butylcarbamate, bethoxazin, o-phthaldialdehyde, 2,2-dibromo-3-nitrile-propionamide, 1,2-dibromo-2,4-dicyanobutane, 1,3-bis(hydroxymethyl)-5,5-dimethylimidazolidine-2,4-dione (DMDMH), tetramethylolacetylenediurea (TMAD), ethyleneglycolhemiformal, p-hydroxybenzoic acid, carbendazim, chlorophen, 3-methyl-4-chlorophenol, o-phenylphenol.

Apart from with the abovementioned fungicides and bactericides, mixtures with a good efficacy are, moreover, also prepared with other active compounds:

insecticides/acaricides/nematicides:
abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtin, azinphos A, azinphos M, azocyclotin,

*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrilfluoron, bromophos A, bromophos M, bufencarb, buprofezin, butathiophos, butocarboxim, butoxycarboxim, cadusafos, carbaryl, carbofuran, carbophenothion, carbosulfan, cartap, quinomethionate, cloethocarb, 4-chloro-2-(2-chloro-2-methylpropyl)-5-[(6-iodo-3-pyridinyl)methoxy]-3 (2H)-pyridazinone (CAS RN: 120955-77-3), chlordane, chlorethoxyfos, chlorfenapyr, chlorfenvinphos, chlorfluazuron, chlormephos, N-[(6-chloro-3-pyridinyl)methyl]-N'-cyano-N-methylethane-imidamide, chlorpicrin, chlorpyrifos A, chlorpyrifos M, cis-resmethrin, clocythrin, clothiazoben, cypophenothrin, clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl (4-ethoxyphenyl)silylmethyl-3-phenoxybenzyl ether, dimethylvinphos, dioxathion, disulfaton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenflutbrin, fenitrothion, fenobucarb, fenothiocarb, fenoxycarb, fenpropathrin, fenpyrad, fenpyroximate, fensulfothion, fenthion, fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan, fosthiazate, fubfenprox, furathiocarb, halofenozide, HCH, (CAS RN: 58-89-9), heptenophos, hexaflumuron, hexythiazox, hydramethylnon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, kadedrin lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxiectin, naled, NI 125, nicotine, nitenpyram, noviflumuron, omethoate, oxamyl, oxydemethon M, oxydeprofos, parathion A, parathion M, penfluron, permethrin, 2-(4-phenoxyphenoxy)ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium, quinalphos, resmethrin, rotenone, salithion, sebufos, silafluofen, spinosad, spirodiclofen, spiromesifen, sulfotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron, trichlorfon, trifumuron, trimethacarb, vamidothion, xylylcarb, zetamethrin;

molluscicides:

fentin acetate, metaldehyde, methiocarb, niclosamide;

herbicides and algicides:

acetochlor, acifluorfen, aclonifen, acrolein, alachlor, alloxydim, ametryn, amidosulfuron, amitrole, ammonium sulfamate, anilofos, asulam, atrazine, azafenidin, aziptrotryne, azimsulfuron, benazolin, benfluralin, benfuresate, bensulfuron, bensulfide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulfuron, chlorthal, chlorthiamid, cinmethylin, cinosulfuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenarnid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, fluorochloridone, fluoroxypyr, fomesafen, fosamine, fosametine, flamprop-isopropyl, flamprop-isopropyl-L, flufenpyr, flumiclorac-pentyl, flumipropyn, flumioxzim, flurtamone, flumioxzim, flupyrsulfuron-methyl, fluthiacet-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron, imazomox, isoxaflutole, imazapic, ketospiradox, lactofen, lenacil, linuron, MCPA, MCPA-hydrazide, MCPA-thioethyl, MCPB, mecoprop, mecoprop-P, mefenacet, mefluidide, mesosulfuron, metam, metamifop, metamitron, metazachlor, methabenzthiazuron, methazole, methoroptryne, methyldymron, methyl isothiocyanate, metobromuron, metoxuron, metribuzin, metsulfuron, molinate, manolide, monolinuron, MSMA, metolachlor, metosulam, metobenzuron, naproanilide, napropamide, naptalam, neburon, nicosulfuron, norflurazon, sodium chlorate, oxadiazon, oxyfluorfen, oxysulfuron, orbencarb, oryzalin, oxadiargyl, propyzamide, prosulfocarb, pyrazolate, pyrazosulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulfuron, prodiamine, profoxydim, prometryn, propachlor, propanil, propaquizafob, propazine, propham, propisochlor, pyriminobac-methyl, pelargonic acid, pyrithiobac, pyraflufen-ethyl, quinmerac, quinocloamine, quizalofop, quizalofop-P, quinchlorac, rimsulfuron sethoxydim, sifuron, simazine, simetryn, sulfosulfuron, sulfometuron, sulfentrazone, sulcotrione, sulfosate, tar oils, TCA, TCA-sodium, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluoralin, tycor, thdiazimin, thiazopyr, triflusulfuron, vernolates.

The present invention further provides the use of azole compounds of the formula (I) for stabilizing iodine-containing biocides against chemical degradation reactions. The materials to be protected from degradation may in principle be any iodine-containing active compounds.

Preference is given to the inventive use for stabilizing the iodine-containing biocides set out above as being preferred and particularly preferred.

The present invention further provides the use of azole compounds of the formula (I) as stabilizers in formulations comprising iodine-containing biocides and in technical products to counter chemical degradation reactions and colour changes.

The azole compounds of the formula (I) can be used in particular for suppressing or at least retarding the chemical degradation of iodine-containing biocides in active compound formulations, more particularly coating materials such as paints, varnishes, primers, impregnating systems, stains and other industrial materials. The azole compounds of the formula (I) which can be used in accordance with the invention for stabilizing iodine-containing biocides have a good stabilizing activity especially in alkyd resin-based systems such as coating materials which comprise transition metal dryers.

The present invention further provides the use of azole compounds of the formula (I) for stabilizing iodine-containing biocides in alkyd resin-based coating materials which comprise transition metal dryers.

The coating materials used in accordance with the invention are especially paints, varnishes, primers, impregnating systems and stains which comprise binders based on alkyd resins.

The alkyd resins present in the coating materials are generally polycondensation resins formed from polyols, polybasic carboxylic acids and/or their anhydrides and fatty oils, or free natural and/or synthetic fatty acids. The alkyd resins may optionally have been chemically modified as well.

The stated polyols are preferably glycerol, pentaerythritol, trimethylolethane, trimethylolpropane and various diols such as ethane-/propanediol, diethylene glycol, neopentyl glycol.

The stated polybasic carboxylic acids and/or their anhydrides are preferably phthalic acid, phthalic anhydride, maleic anhydride, isophthalic acid, terephthalic acid, trimellitic anhydride, adipic acid, azelaic acid or sebacic acid.

The stated oils or fatty acids are generally linseed oil, oiticica oil, tung oil, soya oil, sunflower oil, safflower oil, ricinene oil, tall oil, castor oil, coconut oil, peanut oil, their fatty acids, and also synthetic monocarboxylic acids.

The alkyd resins can optionally also be modified with natural resins, phenolic resins, acrylic resins, styrene, epoxy resins, silicone resins, isocyanates, polyamides or aluminium alkoxides.

The alkyd resins generally have a molar mass of 500 to 100 000. The molar mass is preferably 1000 to 50 000 and more preferably 1500 to 20 000.

The alkyd resins are generally present at 1% to 80%, preferably at 2% to 70% and with particular preference at 3% to 60% by weight in the coating materials, preferably paints, varnishes, primers, impregnating systems or stains.

The transition metal dryers are used in order to accelerate the drying and the curing of oxidatively drying alkyd resin paints. Used here in accordance with the invention preferably are the salts of transition metals of groups Vb, VIb, VIIb, VIII and Ib of the chemical periodic system. Preferably they are the salts of cobalt, manganese, vanadium, nickel, copper and iron, more particularly cobalt, manganese, iron and vanadium. In this context they are not necessarily used only alone, but in some cases also in combination with non-transition metal salts, such as lead, calcium or zirconium, for example.

The transition metal salts are generally composed of the salts of the stated transition metals that are soluble in organic solvents. In principle they may be the salts of all carboxylic acids that have good compatibility with the alkyd resin binders and that ensure sufficient solubility of the metal salt. Preference is given to using the transition metal salts of fatty acids, such as oleates or linoleates, of resin acids, such as resinates, or salts of 2-ethylhexanoic acid (octoates). Preferred transition metal dryers are cobalt octoate and cobalt naphthenate.

The amounts of dryers in the coating materials based on alkyd resins can be varied within a wide range and are guided, for example, by the nature and concentration of the alkyd resin binder and the other paint constituents and also the desired drying characteristics of the paint. The amount of dryers required can be determined by means of routine experiments. Generally speaking, 0.001% to 1%, preferably 0.005% to 0.5% and very preferably 0.01% to 0.1% by weight of dryer is used, based in each case on the amount of binder.

In the context of the inventive use, generally 1% to 150% by weight of at least one compound of the formula (I), preferably 2% to 100% by weight, more particularly 5% to 80% by weight, based on the iodine-containing biocide, is added.

The iodine-containing biocides for stabilization in the context of the inventive use are the compounds set out specifically and generally above. The inventive use of azole compounds of the formula (I) is used in particular to stabilize IPBC in alkyd resin-based coating materials which comprise transition metal dryers.

In the context of the inventive use it is preferred to employ coating materials with the following composition:
Colour pigments: generally 0% to 50%, preferably 0% to 45%, with particular preference 0% to 40% by weight.
Alkyd resin binder: generally 1% to 80%, preferably 2% to 70%, with particular preference 3% to 60% by weight.
Iodine-containing biocide: generally 0.01% to 5%, preferably 0.05% to 3%, with particular preference 0.1% to 2% by weight.
Compound of formula (I): generally 0.001% to 5%, preferably 0.05% to 3%, with particular preference 0.01% to 2% by weight.

The coating materials may further comprise fillers, anti-skinning agents, rheological additives such as anti-settling agents and thixotropic agents, for example, further biocides such as fungicides, bactericides, anti-fouling agents and algicides, solvents, in-process additives, plasticizers, UV stabilizers and heat stabilizers, and corrosion inhibitors, in typical amounts known to the person skilled in the art.

Iodine-containing biocides are degraded in particular in the presence of the dryers described in more detail above. Although the strongest effects are observed in the presence of these dryers, a series of other paint components also have a destabilizing effect on iodine-containing biocides. These include organic and inorganic pigments, fillers, anti-skinning agents, rheological additives such as anti-settling agents and thixotropic agents, for example, further biocides such as fungicides, bactericides, anti-fouling agents and algicides, solvents, in-process additives, plasticizers, UV stabilizers and heat stabilizers, corrosion inhibitors, etc. Here as well the imidazoles, triazoles or tetrazoles of the formula (I) display a strongly stabilizing effect.

The stabilizing effect in accordance with the invention of azole compounds of the formula (I) is, however, not restricted solely to active compound formulations, paints, varnishes and stains, but also includes the stabilization of iodine-containing biocides in other media, such as, for example, plastics, sealants, adhesives, sizes, cooling lubricants, active compound concentrates and formulations.

The stabilizing effect of the azole compounds of the formula (I) is independent of the way in which they are added. For example, the stabilizer can be added directly or as a solution, suspension or emulsion to the medium containing the iodine-containing biocide. Alternatively the stabilizer can be added to the biocide formulation or to the biocide concentrate, which additionally has the advantage that the iodine-containing biocide is protected against degradation not only in the eventual medium but also in the active compound formulation itself.

In addition it is also possible, in the use of the invention, to add further stabilizers as well, such as, for example, the chelating reagents specified in WO 98/22543 or the organic epoxides specified in WO 00/16628. In this case, synergistic effects are often observed.

An additional possibility, in the use of the invention, is also to add one or more stabilizers from the group of antioxidants, free-radical scavengers and UV absorbers, which in some cases exhibit synergistic activities.

Examples of other stabilizers include the following: sterically hindered phenols, such as 2,6-di-tert-butyl-4-methylphenol, 2-tert-butyl-4,6-dimethylphenol, 2,6-di-cyclopentyl-4-methyl-phenol, 2-(α-methylcyclohexyl)-4,6-dimethylphenol, 2,6-di-octadecyl-4-methylphenol or 2,6-di-tert-butyl-4-methoxymethylphenol, diethyl (3,5-di-tert-butyl-4-hydroxybenzyl)phosphonate, 2,4-dimethyl-6-(1-methylpentadecyl)phenol, 2-methyl-4,6-bis[(octylthio)methyl]phenol, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,2'-thiobis(6-tert-butyl-4-methylphenol), 2,2'-thio-bis(4-octylphenol), 4,4'-thiobis(6-tert-butyl-3-methylphenol), 4,4'-thiobis(6-tert-butyl-2-methyl-phenol), 2,2'-methylenebis(6-tert-butyl-4-methylphenol), 2,2'-methylenebis(4-methyl-6-cyclohexyl-phenol), 2,2'-methylenebis(4,6-di-tert-butylphenol), 2,2'-ethylidenebis(4,6-di-tert-butylphenol), 4,4'-methylenebis(2,6-di-tert-butylphenol), 4,4'-methylenebis(6-tert-butyl-2-methylphenol), 1,1-bis(5-tert-butyl-4-hydroxy2-methylphenyl)butane, 1,1,3-tris(5-tert-butyl-4-hydroxy-2-methyl-phenyl)butane, 1,3,5-tri(3,5-di-tert-butyl-4-hydroxybenzyl)-2,4,6-trimethylbenzene, isooctyl 3,5-di-tert-butyl-4-hydroxybenzylmercaptoacetate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 1,3,5-tris[(3,5-di-tert-butyl-4-hydroxyphenyl) propionyloxyethyl] isocyanurate, dioctadecyl 3,5-di-tert-butyl-4-hydroxybenzylphosphonate, calcium monoethyl 3,5-di-tert-butyl-4-hydroxybenzylphosphonate, N,N'-di-(3,5-di-tert-butyl-4-hydroxyphenylpropionyl) hexamethylenediamine, N,N'-di-(3,5-di-tert-butyl-4-hydroxyphenylpropionyl)trimethylenediamine, N,N'-di-(3,5-di-tert-butyl-4-hydroxyphenylpropionyl)hydrazine, 3,9-bis[1,1-dimethyl-2-[(3-tert-butyl-4-hydroxy-5-methylphenyl)propionyloxy]ethyl]-2,4,8,10-tetraoxaspiro[5.5]undecane, bis[3,3-bis(4'-hydroxy-3'-tert-butylphenyl) butanoic acid]ethylene glycol ester, 2,6-bis[[3-(1,1-dimethylethyl)-2-hydroxy-5-methylphenyl]octahydro-4,7-methano-1H-indenyl]-4-methylphenol (=Wingstay 1), 2,4-bis n-octylthio)-6-(3,5-di-tert-butyl-4 hydroxyphenylamino)-s-triazine, N-(4-hydroxyphenyl)octadecaneamide, 2,4-di-tert-butylphenyl 3',5'-di-tert-butyl-4'-hydroxy-benzoate, (benzoic acid, 3,5-bis(1,1-dimethylethyl)-4-hydroxy-, hexadecyl ester), 3-hydroxyphenyl benzoate, 2,2'-methylenebis(6-tert-butyl-4-methylphenol) monoacrylate, 2-(1,1-dimethylethyl)-6-[1-[3-(1,1-dimethylethyl)-5-(1,1-dimethylpropyl)-2-hydroxyphenyl]ethyl]-4-(1, 1-dimethylpropyl)phenyl ester, Esters of β-(3,5-di-tert-butyl-4-hydroxyphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide.

Esters of β-(5-tert-butyl-4-hydroxy-3-methylphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide.

Hindered amines, such as bis(1,2,2,6,6-pentamethyl-4-piperidyl) 2-(3,5-di-tert-butyl-4-hydroxybenzyl)-2-butylmalonate, bis(2,2,6,6-tetramethyl-4-piperidyl)decanedioate, dimethyl succinate-1-(2-hydroxyethyl)-4-hydroxy-2,2,6,6-tetramethylpiperidine copolymer, poly[[6-[(1,1,3,3-tetramethylbutyl)amino]-1,3,5-triazine-2,4-diyl][(2,2,6,6-tetramethyl-4-piperidyl)imino]hexamethylene[(2,2,6,6-tetramethyl-4-piperidyl)imino]] (CAS No. 71878-19-8), 1,5,8,12-tetrakis[4,6-bis(n-butyl-n-1,2,2,6,6-pentamethyl-4-piperidylamino)-1,3,5-triazin-2-yl]-1,5,8,12-tetraazadodecane (CAS No. 106990-43-6), bis(1,2,2,6,6-pentamethyl-4-piperidyl)decanedioate, bis(1,2,2,6,6-pentamethyl-4-piperidyl) 2-(3,5-di-tert-butyl-4-hydroxybenzyl)-2-butylmalonate, decanedioic acid, bis(2,2, 6,6-tetramethyl-4-piperidinyl) ester, reaction products with tert-butyl hydroperoxide and octane (CAS No. 129757-67-1), Chimasorb 2020 (CAS No. 192268-64-7), poly[[6-morpholino-1,3,5-triazine-2,4-diyl]-[(2,2,6,6-tetramethyl-4-piperidinyl)imino]-1,6-hexanediyl[(2,2,6,6-tetramethyl-4-piperidinyl)-imino]], poly[[6-(4-morpholinyl)-1,3,5-triazine-2,4-diyl][1,2,2,6,6-pentamethyl-4-piperidinyl)-imino]-1,6-hexanediyl[(1,2,2,6,6-pentamethyl-4-piperidinyl)imino]] (9CI), 3-dodecyl-1-(2,2,6,6-tetramethyl-4-piperidyl)pyrrolidine-2,5-dione, 3-dodecyl-1-(1,2,2,6,6-pentamethylpiperidin-4-yl)-pyrrolidine-2,5-dione, 4-octadecanoyloxy-2,2,6,6-tetramethylpiperidine, poly[[6-(cyclohexyl-amino)-1,3,5-triazine-2,4-diyl][(2,2,6,6-tetramethyl-4-piperidinyl)imino]-1,6-hexanediyl[(2,2,6,6-tetramethyl-4-piperidinyl)imino]], 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-(CAS No. 109423-00-9), N,N'-bis(formyl)-N,N'-bis(2,2,6,6-tetramethyl-4-piperidyl)-1,6-hexanediamine, N-(tetramethyl-4-piperidinyl)maleimide-C20-24-α-olefin copolymer (CAS No. 199237-39-3), tetrakis(1,2,2,6,6-pentamethyl-4-piperidyl) 1,2,3,4-butanetetracarboxylate, tetrakis(2,2,6,6-tetramethyl-4-piperidyl) 1,2,3,4-butanetetracarboxylate, 1,2,2,6,6-pentamethyl-4-piperidinyl tridecyl 1,2,3,4-butanetetracarboxylate, (1,2,3,4-butanetetracarboxylic acid, 2,2,6,6-tetramethyl-4-piperidinyl tridecyl ester), (2,4,8,10-tetraoxaspiro[5.5]undecane-3,9-diethanol,β,β,β', β'-tetramethyl-, polymer with 1,2,3,4-butanetetracarboxylic acid) (CAS No. 115055-30-6), 2,2,4,4-tetramethyl-21-oxo-7-oxa-3,20-diazadispiro[5.1.11.2]heneicosane, (7-oxa-3,20-diazadispiro[5.1.11.2]heneicosane-20-propanoic acid, 2,2,4, 4-tetramethyl-21-oxo-, tetradecyl ester), (7-oxa-3,20-diazadispiro-[5.1.11.2]heneicosan-21-one, 2,2,4,4-tetramethyl-20-(oxiranylmethyl)-), (propanamide, N-(2,2,6, 6-tetramethyl-4-piperidinyl)-3-[(2,2,6,6-tetramethyl-4-piperidinyl)amino]-), (1,3-propane-diamine, N,N"'-1,2-ethanediylbis-, polymer with 2,4,6-trichloro-1,3,5-triazine, reaction products with N-butyl-2,2,6,6-tetramethyl-4-piperidinamine) (CAS No. 136504-96-6), 1,1'-ethylene-bis(3,3, 5,5-tetramethyl-2-piperazinone), (piperazinone, 1,1',1"-[1,3, 5-triazine-2,4,6-triyltris-[(cyclohexylimino)-2,1-ethanediyl]]tris[3,3,5,5-tetramethyl-), (7-oxa-3,20-diazadispiro[5.1.11.2]-heneicosane-20-propanoic acid, 2,2, 4,4-tetramethyl-21-oxo-, dodecyl ester), 1,1-bis(1,2,2,6,6-pentamethyl-4-piperidyloxycarbonyl)-2-(4-methoxyphenyl) ethene, (2-propenoic acid, 2-methyl-, methyl ester, polymer with 2,2,6,6-tetramethyl-4-piperidinyl 2-propenoate) (CAS No. 154636-12-1), (propanamide, 2-methyl-N-(2,2,6,6-tetramethyl-4-piperidinyl)-2-[(2,2,6,6-tetramethyl-4-piperidinyl)amino]-), (D-glucitol, 1,3:2,4-bis-O-(2,2,6,6-tetramethyl-4-piperidinylidene)-) (CAS No. 99473-08-2), N,N'-bis (2,2,6,6-tetramethyl-4-piperidinyl)isophthalamide, 4-hydroxy-2,2,6,6-tetramethylpiperidine, 1-allyl-4-hydroxy-2,2,6,6-tetramethylpiperidine, 1-benzyl-4-hydroxy-2, 2,6,6-tetramethylpiperidine, 1-(4-tert-butyl-2-butenyl)-4-hydroxy-2,2,6,6-tetramethylpiperidine, 4-stearoyloxy-2,2,6,6-tetramethylpiperidine, 1-ethyl-4-salicyloyloxy-2,2,6,6-tetramethylpiperidine, 4-methacryloyloxy-1,2,2,6,6-pentamethylpiperidine, 1,2,2,6,6-pentamethylpiperidin-4-yl β-(3,5-ditert-butyl-4-hydroxyphenyl)propionate, 1-benzyl-2,2,6,6-tetramethyl-4-piperidinyl maleate, (di-2,2,6,6-tetramethylpiperidin-4-yl) adipate, (di-2,2,6,6-tetramethylpiperidin-4-yl) sebacate, (di-1,2,3,3,6-tetramethyl-2,6-diethylpiperidin-4-yl) sebacate, (di-1-allyl-2,2,6,6-tetramethylpiperidin-4-yl) phthalate, 1-propargyl-4-β-cyanoethyl-oxy-2,2,6,6-tetramethylpiperidine, 1-acetyl-2,2,6,6-tetramethylpiperidin-4-yl acetate, trimellitic acid tri(2,2,6,6-tetramethylpiperidin-4-yl) ester, 1-acryloyl-4-benzyloxy-2,2,6,6-tetramethylpiperidine, dibutyl-malonic acid di(1,2,2,6,6-pentamethylpiperidin-4-yl) ester, butyl(3,5-di-tert-butyl-4-hydroxybenzyl)malonic acid di(1,2,2,6,6-pentamethylpiperidin-4-yl) ester, dibenzylmalonic acid di(1,2,2,6,6-pentamethylpiperidin-4-yl) ester, dibenzylmalonic acid di(1,2,3,6-tetramethyl-2,6-diethylpiperidin-4-yl) ester, hexane-1',6'-bis-(4-carbamoyloxy-1-n-butyl-2,2,6,6-tetramethylpiperidine), toluene-2',4'-bis(4-carbamoyloxy-1-n-propyl-2,2,6,6-tetramethylpiperidine), dimethyl-bis(2,2,6,6-tetramethylpiperidine-4-oxy)silane, phenyl-tris(2,2,6,6-tetramethylpiperidine-4-oxy)silane, tris(1-propyl-2,2,6,6-tetramethyl-piperidin-4-yl) phosphite, tris(1-propyl-2,2,6,6-tetramethylpiperidin-4-yl) phosphate, phenyl[bis(1,2,2,6,6-pentamethylpiperidin-4-yl)phosphonate, di(1,2,2,6,6-pentamethylpiperidin-4-yl) sebacate, N,N'-bis(2,2,6,6-tetramethylpiperidin-4-yl)hexamethylene-1,6-diamine, N,N'-bis(2,2,6,6-tetramethylpiperidin-4-yl)hexamethylene-1,6-diacetamide, 1-acetyl-4-(N-cyclohexylacetamido)-2,2,6,6-tetramethylpiperidine, 4-benzylamino-2,2,6,6-tetramethylpiperidine, N,N'-bis(2,2,6,6-tetramethylpiperidin-4-yl)-N,N'-dibutyladipamide, N,N'-bis(2,2,6,6-tetramethylpiperidin-4-yl)-N,N'-dicyclohexyl(2-hydroxypropylene), N,N'-bis(2,2,6,6-tetramethylpiperidin-4-yl)-p-xylylenediamine, 4-(bis-2-hydroxy-ethyl)amino-1,2,2,6,6-pentamethylpiperidine, 4-(3-methyl-4-hydroxy-5-tert-butyl-benzoic-acidamido)-2,2,6,6-tetramethylpiperidine, 4-methacrylamino-1,2,2,6,6-pentamethylpiperidine, 9-aza-8,8,10,10-tetramethyl-1,5-dioxaspiro[5.5]undecane, 9-aza-8,8,10,10-tetramethyl-3-ethyl-1,5-dioxaspiro[5.5]undecane, 8-aza-2,7,7,8,9,9-hexamethyl-1,4-dioxaspiro[4.5]decane, 9-aza-3-hydroxymethyl-3-ethyl-8,8,9,10,10-pentamethyl-1-5-dioxaspiro[5.5]undecane, 9-aza-3-ethyl-3-acetoxymethyl-9-acetyl-8,8,10,10-tetramethyl-1,5-dioxaspiro[5.5]undecane, 2,2,6,6-tetramethylpiperidine-4-spiro-2'-(1',3'-dioxane)-5'-spiro-5''-(1'',3''-dioxane)-2''-spiro-4'''-(2''',2''',6''',6'''-tetramethylpiperidine)-3-benzyl-1,3,8-triaza-7,7,9,9-tetra-methyl-spiro[4.5]decane-2,4-dione, 3-n-octyl-1,3,8-triaza-7,7,9,9-tetramethyl-spiro-[4.5]decane-2,4-dione, 3-allyl-1,3,8-triaza-1,7,7,9,9-pentamethyl-spiro[4.5]decane-2,4-dione, 3-glycidyl-1,3,8-triaza-7,7,8,9,9-pentamethyl-spiro[4.5]decane-2,4-dione, 2-isopropyl-7,7,9,9-tetramethyl-1-oxa-3,8-diaza-4-oxyspiro[4.5]decane, 2-butyl-7,7,9,9-tetramethyl-1-oxa-3,8-diaza-4-oxyspiro[4.5]decane, 2-isopropyl-7,7,9,9-tetramethyl-1-oxa-4,8-diaza-oxyspiro[4.5]decane, 2-butyl-7,7,9,9-tetramethyl-1-oxa-4,8-diaza-3-oxyspiro[4.5]decane, bis[β-(2,2,6,6-tetramethylpiperidino)ethyl]sebacate, α-(2,2,6,6-tetramethylpiperidino)acetic acid n-octyl ester, 1,4-bis(2,2,6,6-tetramethylpiperidino)-2-butene, N-hydroxymethyl-N'-2,2,6,6-tetramethylpiperidin-4-ylurea, N-methoxymethyl-N'-2,2,6,6-tetramethylpiperidin-4-ylurea, N-methoxymethyl-N'-n-dodecyl-N'-2,2,6,6-tetramethylpiperidin-4-ylurea, O-(2,2,6,6-tetramethylpiperidin-4-yl)-N-methoxymethylurethane, phosphites and phosphonates, such as
tris(nonylphenyl) phosphite, tris(2,4-di-tert-butylphenyl) phosphite, bis(2,4-di-tert-butylphenyl) pentaerythritol diphosphite, bis(2,6-di-tert-butyl-4-methylphenyl)pentaerythritol diphosphite, 2,2'-methylenebis(4,6-di-tert-butylphenyl) octyl phosphite, tetrakis(2,4-di-tert-butylphenyl) [1,1'-biphenyl]-4,4'-diylbisphosphonite, 2,2'ethylidenebis(4,6-di-tert-butylphenyl) fluorophosphite, dioctadecyl pentaerythritol diphosphonite, 2-[[2,4,8,10-tetrakis(1,1-dimethyl-ethyl)dibenzo[d,f][1,3,2]dioxaphosphin-6-yl]oxy]-N,N-bis[2,4,8,10-tetrakis(1,1-dimethyl-ethyl)dibenzo[d,f][1,3,2]dioxaphosphin-6-yl]oxy]ethyl]ethanamine (CAS No. 80410-33-9), bis(2,4-di-tert-butyl-6-methylphenyl)ethyl phosphite, 2,4,6-tri-tert-butylphenyl-2-butyl-2-ethyl-1,3-propanediol phosphite, bis(2,4-dicumylphenyl) pentaerythritol diphosphite, hydroxylamines, such as
amines, bis(hydrogenated tallow alkyl), oxidized,
secondary arylamines, such as
N-(2-naphthyl)-N-phenylamine, 2,2,4-trimethyl-1,2-dihydroquinoline polymer (CAS No. 26780-96-1), N-2-propyl-N'-phenyl-p-phenylenediamine, N-(1-naphthyl)-N-phenylamine, (benzenamine, N-phenyl-, reaction products with 2,4,4-trimethylpentene) (CAS No. 68411-46-1), 4-(1-methyl-1-phenylethyl)-N-[4-(1-methyl-1-phenylethyl)phenyl]aniline.

Lactones and benzofuranones, such as
Irganox HP 136 (CAS No. 181314-48-7)
thioethers and thioesters, such as
distearyl 3,3-thiodipropionate, dilauryl 3,3'-thiodipropionate, ditetradecyl thiodipropionate, di-n-octadecyl disulphide.

UV absorbers, such as
(methanone, [methylenebis(hydroxymethoxyphenylene)]bis[phenyl-), (methanone, [1,6-hexane-diylbis[oxy(2-hydroxy-4,1-phenylene)]]bis[phenyl-), 2-benzoyl-5-methoxyphenol, 2,4-dihydroxy-benzophenone, 2,2'-dihydroxy-4-methoxybenzophenone, 2-hydroxy-4-octyloxybenzophenone, 2-hydroxy-4-dodecyloxybenzophenone, 2-(2-hydroxy-4-hexyloxyphenyl)-4,6-diphenyl-1,3,5-triazine, 2,4-bis(2,4-dimethylphenyl)-6-(2-hydroxy-4-octyloxyphenyl)-1,3,5-triazine, 2-ethoxy-2'-ethyloxalic acid bisanilide, N-(5-tert-butyl-2-ethoxyphenyl)-N-(2-ethylphenyl)-oxamide, dimethyl (p-methoxybenzylidene)malonate, 2,2'-(1,4-phenylene)bis[3,1-benzoxazin-4-one], N'-(4-ethoxycarbonylphenyl)-N-methyl-N-phenylformamidine, 4-methoxycinnamic acid 2-ethylhexyl ester, 4-methoxycinnamic acid isoamyl ester, 2-phenylbenzimidazole-5-sulphonic acid, 2-cyano-3,3-diphenylacrylic acid 2-ethylhexyl ester, 2-ethylhexyl salicylate, 3-(4-methyl-benzylidene)bornan-2-one, complexing agents, such as
ethylenediaminetetraacetate (EDTA), ethylenediamine, acetylacetone, nitrotriacetic acid, ethylene glycol bis(β-aminoethyl ether)-N,N-tetraacetic acid, 2,2'-bipyridine, 4,4'-dimethyl-2,2'-bipyridine, 2,2'6',2''-terpyridine, 4,4'-diphenyl-2,2'-bipyridine, 2,2'-bipyridine-3,3'-diol, 1,10-phenanthroline, 4-methyl-1,10-phenanthroline, 5-methyl-1,10-phenanthroline, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,4,7,9-tetramethyl-1,10-phenanthroline, N,N,N',N'-tetramethylethylene-diamine, 2-hydroxyquinoline, 8-hydroxyquinoline, 2-hydroxy-4-methylquinaldine, 5-chloro-8-hydroxyquinoline, 5,7-dichloro-8-hydroxyquinoline, 2,4-quinolinediol, 2-quinalonethiol, 8-quinolinethiol, 8-aminoquinoline, 2,2'-biquinoline, 2-quinoxalinol, 3-methyl-2-quinoxalinol, 2,3-dihydroxyquinoxaline, 2-mercaptopyridine, 2-dimethylaminopyridine, 1,2-bis(dimethyl-phosphino)ethane, 1,2-bis(diphenylphosphino)ethane, 1,3-bis(diphenylphosphino)propane, 1,4-bis(diphenylphosphino)butane, polyaspartic acid, iminodisuccinate, or else further imidazoles, triazoles or tetrazoles of the formula (I).

The azole compounds of the formula (I), where appropriate in a mixture with one or more of the stabilizers mentioned above, protect the iodine-containing biocides from decomposition not only in the liquid paint, but also, additionally, have a stabilizing activity on the iodine-containing biocides in the dry paint film and an activity against decomposing effects induced by light.

The amount of azole compounds of the formula (I) needed in order to stabilize the iodine-containing biocide in a technical medium can be determined by means of routine experiments and is guided both by the nature and concentration of the iodine-containing biocide and by the nature and amount of additives in the technical medium, such as the paint or formulation.

In the case of alkyd resin-based systems such as coating materials, the amount of azole compounds of the formula (I) which must be used in order to stabilize is dependent on the nature and amount of the dryer employed, of the alkyd resins, and of further constituents in the paint formulation.

In the case of alkyd resin paints the amount must be set such that, while the iodine-containing biocides do not undergo degradation, the actual effect of the dryer is not suppressed either. In other media, the application amount must be set so that, although stabilization is observed, the properties of the medium are not altered.

In the industrial media the azole compounds of the formula (I) are used generally in concentrations of 0.001% by weight to 5% by weight, based on the total amount of the paint. Preferably the imidazoles, triazoles or tetrazoles of the formula (I) are used in concentrations of 0.005% to 3% and with particular preference between 0.01% and 2% by weight.

In active compound formulations and concentrates, the azole compounds of the formula (I) are used in larger amounts. Use is made in general of 0.5% to 50%, preferably 1% to 40% and with particular preference 2% to 30% by weight of azole compounds of the formula (I), based on the amount of formulation or amount of concentrate.

EXAMPLE A

A solution was prepared in Dowanol TPM (tripropylene glycol methyl ether), containing 10% by weight of iodopropargyl butylcarbamate, 5% by weight of Octasoligen-Cobalt 8 (Borchers, Langenfeld, Germany) and 5% by weight of the azole compounds of the formula (I) specified as a stabilizer in Table 1. The mixture was stored at 40° C. The amount of IPBC was determined by means of HPLC at the beginning and after two weeks.

| Example No. | Stabilizer | Amount of IPBC (start) | Amount of IPBC (2 weeks, 40° C.) | Remark |
|---|---|---|---|---|
| | none | 10.3% | 2.2% | comparison without stabilizer |
| 1 | (triazole-SH) | 10.2% | 9.0% | |
| 2 | (HS-triazole-OH) | 9.9% | 8.9% | |
| 3 | (triazole-NH₂) | 9.7% | 9.5% | |
| 4 | (H₂N-triazole-NH₂) | 9.7% | 9.7% | |

EXAMPLE B

Incorporated by vigorous stirring (using, for example, a dissolver) into a woodstain whose composition was as specified below was 1% of IPBC and the amount specified in the table of azole compound of the formula (I) as a stabilizer. The composition was stored at 40° C. The amount of IPBC was determined by means of HPLC at the beginning and after one month.

| Example No. | Stabilizer | Amount of stabilizer | Amount of IPBC (start) | Amount of IPBC (1 month, 40° C.) | Remark |
|---|---|---|---|---|---|
| | none | | 0.98% | 0.25% | comparison without stabilizer |
| 5 | (triazole-SH) | 0.2% | 0.99% | 0.90% | |

-continued

| Example No. | Stabilizer | Amount of stabilizer | Amount of IPBC (start) | Amount of IPBC (1 month, 40° C.) | Remark |
|---|---|---|---|---|---|
| 6 | 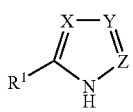 | 0.5% | 1.01% | 0.81% | |
| 7 | | 0.05% | 1.05% | 0.98% | |
| 8 | 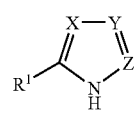 | 0.1% | 1.02% | 0.80% | |

Composition of the preservative woodstain used:

| | |
|---|---|
| Alkydal F 681, 75% strength in white spirit | 28% |
| 2-Phenoxyethanol | 3% |
| Dowanol DPM | 3% |
| Solvesso 150 | 10% |
| BHT, 1% in Kristalloel K 60 | 2% |
| Octa Soligen Co 8% | 0.19% |
| Octa Soligen Zr 18% | 1.4% |
| Kristalloel 60 | 52.41% |

The present invention has been described with reference to specific details and examples of particular embodiments thereof. It is not intended that such details and examples be regarded as limitations upon the scope of the invention except insofar as and to the extent that they are included in the accompanying claims.

As used in this specification and the appended claims, the singular forms "a," "an," and "the" include plural referents unless the content clearly dictates otherwise.

What is claimed is:

1. An active compound mixture comprising at least one iodine-containing biocide selected from the group consisting of iodoalkynyl compounds, compounds in which one or more iodine atoms are bonded to double bound systems and compounds in which one or more iodine atoms are bonded to singly bonded atoms; and at least one azole compound of the formula (I) or tautomer thereof, $$\underset{R^1}{\overset{X-Y}{\underset{\underset{H}{N}}{\bigvee}}}Z \qquad (I)$$

in which
R¹ is hydrogen, hydroxyl, mercapto or optionally substituted amino
and
X, Y and Z independently of one another are N or C—R²,
in which
R² is hydrogen, hydroxyl, mercapto or optionally substituted amino.

2. The mixture according to claim 1 wherein
R¹ is hydrogen, hydroxyl, mercapto, amino, $C_1$-$C_3$-alkylamino.

3. The mixture according to claim 1 or 2, wherein the iodine-containing biocide is one or more iodoalkynyl compounds.

4. The mixture according to claim 1 or 2, characterized in that it contains 0.01%-70% by weight of the iodine-containing biocide and 0.001%-50% by weight of the at least one azole of the formula (I).

5. A microbicidal composition comprising an active compound mixture according to claim 1 or 2, further comprising at least one solvent or diluent.

6. A process for protecting an industrial material from infestation and/or destruction by microorganisms, comprising:
contacting the industrial material with the active compound mixture according to claim 1 or 2.

7. A process for stabilizing an iodine-containing biocide against chemical degradation reactions, comprising:
a) mixing an iodine-containing biocide selected from the group consisting of iodoalkynyl compounds, compounds in which one or more iodine atoms are bonded to double bound systems and compounds in which one or more iodine atoms are bonded to singly bonded atoms and an at least one azole compound of the formula (I) or tautomers thereof, $$\underset{R^1}{\overset{X-Y}{\underset{\underset{H}{N}}{\bigvee}}}Z \qquad (I)$$

in which
R¹ is hydrogen, hydroxyl, mercapto or optionally substituted amino
and
X, Y and Z independently of one another are N or C—R²,
in which
R² is hydrogen, hydroxyl, mercapto or optionally substituted amino.

8. The process according to claim 7, wherein the iodine-containing biocide is stabilized in an industrial material.

9. The process according to claim 8, wherein the industrial material is a paints based on alkyd resin binders comprising transition metal dryers.

10. An industrial material comprising at least one iodine-containing biocide selected from the group consisting of iodoalkynyl compounds, compounds in which one or more iodine atoms are bonded to double bound systems and compounds in which one or more iodine atoms are bonded to singly bonded atoms;
and at least one azole of the formula (I) or tautomer thereof,

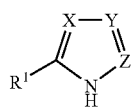

in which
$R^1$ is hydrogen, hydroxyl, mercapto or optionally substituted amino
and
X, Y and Z independently of one another are N or C—$R^2$, in which
$R^2$ is hydrogen, hydroxyl, mercapto or optionally substituted amino.

11. A microbicidal composition comprising an active compound mixture according to claim 1 or 2, further comprising at least one solvent or diluent and processing assistants.

12. The microbicidal composition according to claim 11 further comprising further antimicrobial compounds.

13. The mixture according to claim 3, wherein the iodoalkynyl compounds are selected from the group consisting of 3-iodo-2-propynylpropyl carbamate, 3-iodo-2-propynylbutyl carbamate (IPBC), 3-iodo-2-propynyl-m-chlorophenyl carbamate, 3-iodo-2-propynylphenyl carbamate, 3-iodo-2-propynyl 2,4,5-trichlorophenyl ether, 3-iodo-2-propynyl 4-chlorophenyl formal (IPCF), di(3-iodo-2-propynyl) hexyl dicarbamate, 3-iodo-2-propynyloxyethanol ethylcarbamate, 3-iodo-2-propynyloxyethanol phenyl carbamate, 3-iodo-2-propynylthioxothioethyl carbamate, 3-iodo-2-propynylcarbamic ester (IPC), N-iodpropargyloxycarbonylalanine, N-iodoproparayloxycarbonylalanine ethyl ester, 343-iodopropargyl)benzoxazol-2-one, 3-(3-iodopropargyl)-6-chlorobenzoxazol-2-one, diiodomethyl p-tolyl sulphone, diiodomethyl p-chlorophenyl sulphone, 3-iodo-2-propynyl alcohol, 4-chlorophenyl-3-iodopropargyl formal, 3-bromo-2, 3-diiodo-2-propenyl ethylcarbamate, 2,3,3-triiodoallyl alcohol, 3-bromo-2,3-diiodo-2-propenyl alcohol, 3-iodo-2-propynyl n-hexylcarbamate, and 3-iodo-2-propynyl cyclohexylcarbamate.

14. The mixture according to claim 5, further comprising further antimicrobial compounds.

* * * * *